United States Patent [19]

Casagrande et al.

[11] Patent Number: 4,579,861
[45] Date of Patent: Apr. 1, 1986

[54] ARYLOXYPROPANOLAMINE DERIVATIVES, PHARMACEUTICAL COMPOSITIONS AND ADRENEGIC THEREOF

[75] Inventors: Cesare Casagrande, Arese; Massimo Nicola, Pavia, both of Italy

[73] Assignee: Pierrel S.p.A., Naples, Italy

[21] Appl. No.: 568,598

[22] Filed: Jan. 6, 1984

[30] Foreign Application Priority Data

Jan. 21, 1983 [IT] Italy ............... 19219 A/83

[51] Int. Cl.$^4$ ............... A61K 31/415; C07D 403/30; C07D 233/30
[52] U.S. Cl. ............... 514/392; 548/319; 548/318
[58] Field of Search ............... 548/319, 318; 514/392

[56] References Cited

U.S. PATENT DOCUMENTS 4,319,032 3/1982 Sandri et al. ............... 548/319

OTHER PUBLICATIONS

Noller, Textbook of Organic Chemistry, W. B. Saunders Co., Philadelphia, 1966, p. 226.

Primary Examiner—Henry R. Jiles
Assistant Examiner—Robert C. Whittenbaugh
Attorney, Agent, or Firm—Bucknam and Archer

[57] ABSTRACT

Compounds having general formula I

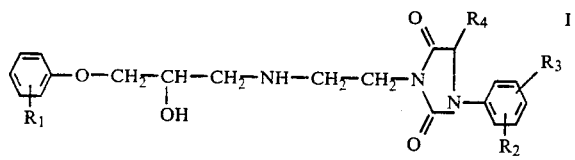

wherein
  $R_1$ is hydrogen, lower alkyl, lower alkoxy, alkyl enoxy, halogen, cyano, carboxyamido or ureido group optionally separated from the phenyl ring by a methylene or ethylene bridge;
  $R_2$ is hydrogen, halogen, lower alkyl or alkoxy;
  $R_3$ is hydrogen, halogen, lower alkyl, lower alkoxy or $R_2$ and $R_3$, taken together, are a methylendioxy group;
  $R_4$ is hydrogen or lower alkyl,
endowed with remarkable cardioselective β-adrenolytic properties, are described.

The process for their preparation and pharmaceutical compositions containing them are also described.

9 Claims, No Drawings

ARYLOXYPROPANOLAMINE DERIVATIVES, PHARMACEUTICAL COMPOSITIONS AND ADRENEGIC THEREOF

The object of the present invention is provided by new aryloxypropanolamine derivatives endowed with potent and selective myocardial β-adrenergic receptors blocking activity.

The compounds according to the present invention have the following general formula I:

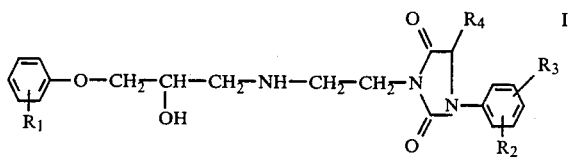

wherein
$R_1$ is hydrogen, lower alkyl, lower alkoxy, alkylenoxy, halogen, cyano, carboxyamido or ureido group optionally separated from the phenyl ring by a methylene or ethylene bridge;
$R_2$ is hydrogen, halogen, lower alkyl or alkoxy;
$R_3$ is hydrogen, halogen, lower alkyl, lower alkoxy or $R_2$ and $R_3$, taken together, are a methylendioxy group;
$R_4$ is hydrogen or lower alkyl.

The R and S forms, as well as their racemic mixture, are also included in the meaning of formula I. Moreover, when $Rr_4$ is different from hydrogen, the compounds of the invention exist in the form of two couples of diastereoisomers which can be separated by fractional crystallization or by chromatographic methods: therefore, the invention includes both the separated couples and their mixtures or the separated optically pure forms.

Finally, another object of the invention is provided by the addition salts of the compounds of formula I with pharmaceutically acceptable acids such as, for instance, hydrochloride, hydrobromide, sulphate or bisulphate, phosphate, acetate, tartrate, citrate, maleate, methansulphonate etc.

Beta-blocker compounds of general formula

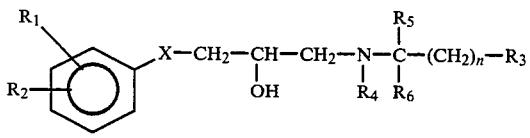

wherein, inter alia, X may be an oxygen atom, $R_1$, $R_4$, $R_5$ and $R_6$ may be hydrogen, n may be 1 and $R_3$ may be an imidazole ring at least partially hydrogenated, linked to the rest of the molecule by means of one of the nitrogen atoms and bearing one or two oxo or thio groups and optionally one or more alkyl substituents, are included within the general meanings of British Pat. No. 1345075. In said patent, besides the fact that the possibility of substitution by a phenyl group of the possible imidazole residue is not even mentioned, it should be pointed out that the compounds having a hydantoin residue in the basic moiety are simply cited and never exemplified, the class of the compounds having a substituted 1-1,2,3,4-tertrahydro-2,4-dioxo-pyrimidine group being preferred.

Some other β-blockers having also an imidazolinone group linked to the amine group by means of an alkylene chain, are described in the German published Patent Application No. 2644833 claiming compounds of general formula

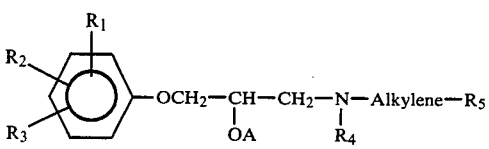

wherein Alkylene means a $C_1$–$C_{12}$ linear or branched alkylene chain, A and $R_4$ may be hydrogen and $R_5$ may represent, inter alia, a 3-phenyl-2-imidazolinone group of formula

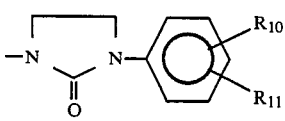

The compounds of the invention are, on the contrary, characterized by the presence of a hydantoin group having a nitrogen atom linked to the propanolamine nitrogen by means of an ethylene group and an optionally substituted phenyl ring on the other nitrogen atom.

The compounds of the invention are easily prepared by reaction of an 1-aryl-3-ethyl hydantoin of formula II with an aryloxy propane derivative of formula III

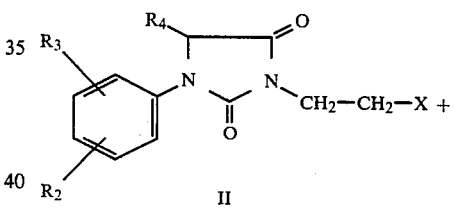

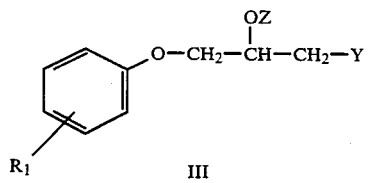

wherein $R_1$, $R_2$, $R_3$ and $R_4$ have the above defined meanings, X is an amine group or an halogen atom, Z is hydrogen, and Y is an optionally protected amine group, or an halogen atom, or Y and Z, taken together, form an epoxidic bond between the oxygen atom and the terminal carbon, with the proviso that one and only one between X and Y must be an amino or protected amino group.

The term "halogen" may include chlorine, bromine, iodine and fluorine but, preferably, it stands for a bromine or a chlorine atom.

"Protected amino group" means an amino group wherein one of the two hydrogen atoms is substituted by a protective groups, as it is known in the art, which can be easily displaced when the reaction is over so as to restore the free amino group.

According to the present invention, preferred protective groups are, for instance, the benzyl, nitrobenzyl, halobenzyl groups, and in general the ring-substituted benzyl groups, and the trytyl group which, when the reaction is over, can be easily displaced by hydrogenolysis in mild conditions.

Generally, the reaction between the hydantoin derivative II and the aryloxypropane derivative III is carried out in the presence of a polar organic solvent, protic or aprotic, such as alcohols, dimethylsulfoxide, dimethylformamide, tetrahydrofuran etc.

The reaction can take place even at room temperature, but, preferably, the reaction mixture is heated up to the reflux temperature in order to increase the reaction rate.

When X or Y are a halogen atom, it is usually necessary either the presence of an excess of the other basic reagent or even better the presence of an additional organic or inorganic base, such as a trialkylamine, pyridine, picoline etc. or an alkaline hydroxide or carbonate as an acceptor of the halogenidric acid forming during the reaction.

On the other hand, when Y and Z taken together form an epoxide bond, generally a slight excess of the epoxide reagent is preferably used.

Moreover, in this case, the reaction can be carried out also in the absence of solvents, by melting together the two reagents.

When the reaction, which is followed by thin layer chromatography, is over, the solvent (when present) is evaporated and the obtained crude product is purified by usual methods such as fractional crystallization or chromatographic techniques.

According to a preferred embodiment of the present invention, the compounds of formula I are prepared by reaction of a 1-aryl-3-(2-aminoethyl)-hydantoin (II, X=NH$_2$) with a 1,2-epoxy-3-phenoxy-propane (III, Y and Z form together an epoxide bond) in the presence of a lower aliphatic alcohol (methanol, ethanol) as a solvent, by refluxing the reaction mixture for some hours.

The solvent is then distilled off and the crude residue so obtained is purified by crystallization or chromatography.

The starting products of formula II can be easily prepared in turn starting from the corresponding N-phenylglycine compounds of formula IV or from a lower alkyl ester thereof.

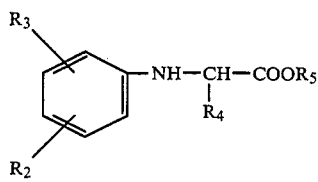

($R_5$ = H or ($C_1$-$C_2$)alkyl)

by reaction with an alkaline cyanate followed by conversion of the so obtained 1-aryl-hydantoin of formula V

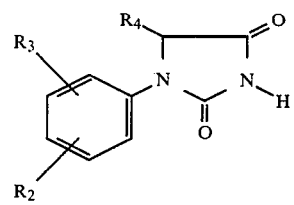

into the desired 1-aryl-3-(2-substituted-ethyl)hydantoin II by reaction with an haloethylene derivative of formula Halo—CH$_2$—CH$_2$—X wherein Halo means an halogen atom and preferably a bromine or chlorine atom and $R_2$, $R_3$, $R_4$ and X have the above defined meanings. These reactions are carried out according to usual methods known in the art.

For instance, good results are obtained by refluxing a slightly acidic aqueous solution of the N-phenylglycine IV and equimolar amounts of potassium cyanate and precipitating the product V, at the end of the reaction by mineral acid acidification. Then, this intermediate can be used as such in the subsequent step providing the reaction with the haloethylene derivative in at least equimolar amounts, in the presence of a strong base such as an alkaline hydroxide or hydride. The reaction is carried out in a polar, protic or aprotic, solvent, preferably an alcohol, by refluxing the reaction mixture for some hours. When the reaction is over the desired product of formula II is recovered according to usual methods.

The starting compounds of formula III are generally known compounds and are prepared according to methods known in literature.

Whereas the single enantiomers having formula I have to be prepared, when $R_4$ is hydrogen, these can be obtained either by stereospecific synthesis starting from the suitable reagent III having the desired configuration (R or S) of the asymmetric carbon atom, or by resolution of the racemic mixture through formation of an addition salt with an optically active organic acid and fractional crystallization of the two diastereoisomeric salts so obtained. In the first instance, the stereospecific synthesis of the reagent III, wherein, according to a preferred embodiment of the invention, Y and Z taken together form an epoxide bond, starts from the two enantiomers of 2,3-isopropylidenglycerol VI (Scheme I) which is reacted with tosyl chloride to give the tosyl-derivative VII, in its turn condensed with the suitable phenol to give VIII. The reaction of the latter with hydrobromic acid in acetic acid yields the bromidrine acetate IX which, by base treatment in phase-transfer catalysis conditions, gives the epoxide III, having R or S conformation depending on the S or R configuration of the starting material.

SCHEME I

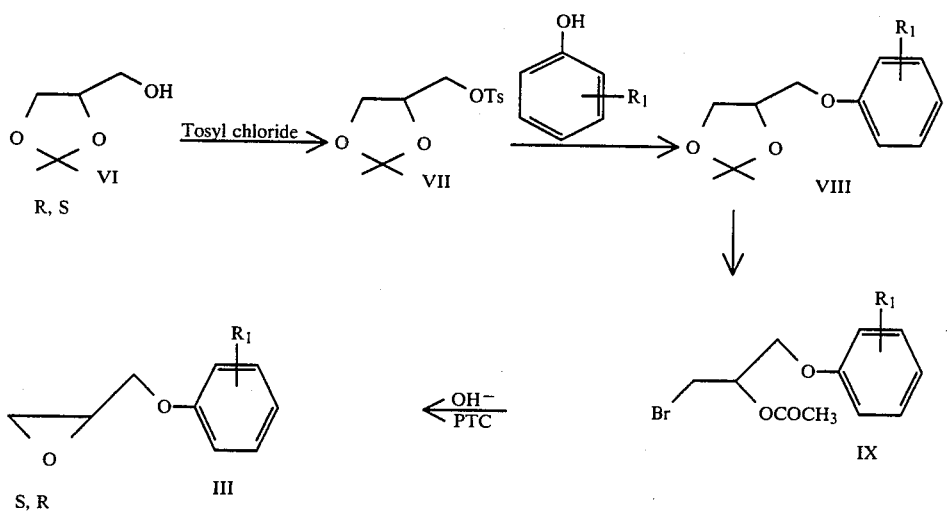

The chiral epoxide III, so obtained, after reaction with the hydantoin derivative II, wherein X is amino, gives the product I having the same configuration. In the second case, optically active organic acids which can be suitably used in the resolution of the racemic base are l-mandelic acid, d-camphorsulfonic acid, d-tartaric acid etc.

When $R_4$ is different from hydrogen, and it is desired to prepare the single enantiomers, it is convenient to carry out a stereospecific synthesis starting from both reagents having the desired configuration. Alternatively, the reaction can be carried out using only one of the two reagents in optically pure form and separating thereafter the two diastereoisomers of formula I which are then obtained by means of usual methods.

The following non limitative examples illustrate the process according to the invention further on.

EXAMPLE 1

1-Phenyl-3-{[2-(3-phenoxy-2-hydroxy)propylamino]ethyl}hydantoin hydrochloride Ia A solution of 1-phenyl-3-(2-aminoethyl)-hydantoin (6.4 g, 29.17 mmoles) and of 1,2-epoxy-3-phenoxypropane (J. Chem. Soc. 95, 1803) (4.38 g, 29.17 mmoles) in methanol (90 ml) was refluxed for three hours.

The solvent was evaporated and the crude product was purified by column chromatography eluting with ethyl acetate/methanol. The solvent was evaporated, the reaction product was treated with acetone and 2N hydrochloric acid was added thereto. The title compound (Ia), melting point 184°–185° C., precipitated.

EXAMPLE 2

In the same way as in Example 1, but reacting the 1-phenyl-3-(2-aminoethyl)hydantoin with 3-(3-methylphenoxy)-1,2-epoxypropane (Chem. Ber. 24, 2146), with 3-(2-cyanophenoxy)-1,2-epoxypropane (Ger. Offen. 2048838), with 3-(2-methylphenoxy)-1,2-epoxypropane (Chem. Ber. 24, 2146) or with 3-(2-chlorophenoxy)-1,2-epoxypropane (C.A.41, 3755h) the compounds Ib, Ic, Io and Ip, whose characteristics are reported in the Table I, were respectively obtained.

EXAMPLE 3

Starting from the 1-(4-chlorophenyl)-3-(2-aminoethyl)-hydantoin and carrying out the reaction as in the Example 1, the compound Id, Ie and If were obtained by reaction respectively with 1,2-epoxy-3-phenoxypropane, 3-(3-methylphenoxy)-1,2-epoxypropane and 3-(2-cyanophenoxy)-1,2-epoxypropane. The characteristics of the products are reported in the Table I.

EXAMPLE 4

In the same way as in Example 1, by reaction of the 1-(3,4-dimethoxyphenyl)-3-(2-aminoethyl)-hydantoin with 1,2-epoxy-3-phenoxypropane, 3-(3-methylphenoxy)-1,2-epoxypropane and 3-(2-cyanophenoxy)-1,2-epoxypropane the compounds Ig, Ih and Ii, whose characteristics are reported in Table I, were respectively obtained.

EXAMPLE 5

1-(4-Methoxyphenyl)-3-{2-[3-(2-cyanophenoxy)-2-hydroxypropyl]aminoethyl}hydantoin hydrochloride Il In the same way as in Example 1, the final product Il, whose characteristics are reported in Table I, was obtained by reaction of the 1-(4-methoxyphenyl)-3-(2-aminoethyl)-hydantoin with 3-(2-cyanophenoxy)-1,2-epoxypropane.

EXAMPLE 6

1-(3,4-Methylendioxyphenyl)-3-{2-[3-(2-cyanophenoxy)-2-hydroxypropyl]aminoethyl}hydantoin hydrochloride Im In the same way as in Example 1, the final product Im, whose characteristics are reported in Table 1, was obtained by reaction of the 1-(3,4-methylendioxxyphenyl)-3-(2-aminoethyl)-hydantoin with 3-(2-cyanophenoxy)-1,2-epoxypropane.

EXAMPLE 7

1-(3-Methoxyphenyl)-3-{2-[3-(2-cyanophenoxy)-2-hydroxypropyl]-aminoethyl}hydantoin hydrochloride In In the same way as in Example 1, the final product In, whose characteristics are reported in Table I, was obtained by reaction of the 1-(3-methoxyphenyl)-3-(2-aminoethyl)-hydantoin with 3-(2-cyanophenoxy)-1,2-epoxy-propane.

chloroform/methanol. 1.4 g of Ic (R isomer) as a base, $[\alpha]_D$ (C=1, EtOH) = +4.14°, were obtained.

From 1 g of base, dissolved in acetone and treated with 2N hydrochloric acid, the hydrochloride was obtained, g 1 $[\alpha]_D$ (C=0.5, MeOH) = +16.57°.

EXAMPLE 10

(S)-(−)-1-Phenyl-3-{2-[3-(2-cyanophenoxy)-2-hydroxypropyl]aminoethyl}hydantoin hydrochloride Ic In the same way as in Example 9, from 1-phenyl-3-(2-aminoethyl)-hydantoin (2.3 g, 10.5 mmoles) and S-(+)-3-(2-cyanophenoxy)-1,2-epoxypropane (1.75 g, 10 mmoles) 1.5 g of Ic (S isomer) as base were obtained, $[\alpha]_D$ (C=1, EtOH) = −2.82.

From 1 g the hydrochloride was prepared, 1 g $[\alpha]_D$ (C=0.5, MeOH) = −15.75°.

TABLE I $$\text{R}_1\text{-C}_6\text{H}_4\text{-OCH}_2\text{CHCH}_2\text{NHCH}_2\text{CH}_2\text{N}\cdots\text{hydantoin ring}\cdots\text{C}_6\text{H}_3(\text{R}_2)(\text{R}_3) \quad \text{I}$$
(with OH on central carbon, ·HCl)

| Compound | $R_1$ | $R_2$ | $R_3$ | m.p. °C. | Formula | Calcd. C | Calcd. H | Calcd. N | Found C | Found H | Found N |
|---|---|---|---|---|---|---|---|---|---|---|---|
| Ia | H | H | H | 184–185 | $C_{20}H_{23}N_3O_4$·HCl | 59.18 | 5.96 | 10.35 | 59.37 | 6.12 | 10.52 |
| Ib | 3-CH$_3$ | H | H | 192–194 | $C_{20}H_{25}N_3O_4$·HCl | 60.06 | 6.24 | 10.00 | 60.00 | 6.36 | 9.85 |
| Ic | 2-CN | H | H | 207–209 | $C_{21}H_{22}N_4O_4$·HCl | 58.54 | 5.38 | 13.00 | 58.61 | 5.45 | 12.89 |
| Id | H | 4-Cl | H | 209–210 | $C_{20}H_{22}ClN_3O_4$·HCl | 54.55 | 5.26 | 9.54 | 54.36 | 5.22 | 9.51 |
| Ie | 3-CH$_3$ | 4-Cl | H | 187–189 | $C_{21}H_{24}ClN_3O_4$·HCl | 55.51 | 5.55 | 9.25 | 55.32 | 5.51 | 9.39 |
| If | 2-CN | 4-Cl | H | 177–179 | $C_{21}H_{21}ClN_4O_4$·HCl·3H$_2$O | 48.56 | 5.43 | 10.79 | 48.20 | 5.63 | 10.91 |
| Ig | H | 3-(OCH$_3$) | 4-(OCH$_3$) | 167–168 | $C_{22}H_{27}N_3O_6$·HCl·H$_2$O | 54.60 | 6.25 | 8.68 | 54.31 | 6.08 | 8.68 |
| Ih | 3-CH$_3$ | 3-(OCH$_3$) | 4-(OCH$_3$) | 153–155 | $C_{23}H_{29}N_3O_6$·HCl | 57.56 | 6.30 | 8.75 | 57.39 | 6.28 | 8.79 |
| Ii | 2-CN | 3-(OCH$_3$) | 4-(OCH$_3$) | 131–133 | $C_{23}H_{26}N_4O_6$·HCl·H$_2$O | 52.42 | 5.93 | 10.63 | 52.63 | 5.74 | 10.70 |
| Il | 2-CN | 4-OCH$_3$ | H | 167–170 | $C_{22}H_{24}N_4O_5$·HCl | 57.33 | 5.47 | 12.15 | 57.40 | 5.33 | 12.09 |
| Im | 2-CN | 3,4-OCH$_2$O— | | 192–194 | $C_{22}H_{22}N_4O_6$·HCl | 55.64 | 4.88 | 11.79 | 55.38 | 4.79 | 11.94 |
| In | 2-CN | 3-OCH$_3$ | H | 179–181 | $C_{22}H_{24}N_4O_5$·HCl | 57.33 | 5.47 | 12.15 | 57.11 | 5.30 | 12.21 |
| Io | 2-CH$_3$ | H | H | 163–166 | $C_{21}H_{25}N_3O_4$·HCl | 60.07 | 6.24 | 10.00 | 59.49 | 6.20 | 9.86 |
| Ip | 2-Cl | H | H | 194–196 | $C_{20}H_{22}ClN_3O_4$·HCl | 54.55 | 5.26 | 9.54 | 54.32 | 5.28 | 9.42 |

EXAMPLE 8

The compound Ia was prepared also in the following way.

A mixture of 1-phenoxy-3-benzylamino-2-propanol (Ann. Inst. Pasteur, 44, 719, 1930) (0.514 g, 2 mmoles)), 1-phenyl-3-(2-bromoethyl)hydantoin (0.566 g, 2 mmoles) and sodium bicarbonate (0.168 g, 2 mmoles) in ethanol (15 ml) was refluxed for 54 hours. The salts were filtered and the mother liquors were evaporated. The residue was crystallized twice from toluene/hexane and transformed into hydrochloride adding 2N hydrochloric acid to the solution of the product in acetone. 160 mg of 1-phenyl-3-{[2-N-benzyl-N-(3-phenoxy-2-hydroxy)propylamino]ethyl}hydantoin. HCl, m.p. (crude) 185 dec., precipitated.

This product (160 mg, 0.32 mmoles) was dissolved in 20 ml of ethanol, 16 mg of 10% palladium on charcoal were added and the mixture was hydrogenated at room temperature and pressure. After 4 hours the debenzylation was complete. Ia (mg 96), m.p. 184°–185°, was obtained.

EXAMPLE 9

(R)-(+)-1-Phenyl-3-{2-[3-(2-cyanophenoxy)-2-hydroxypropyl]aminoethyl}hydantoin hydrochloride Ic (R)-(−)-3-(2-Cyanophenoxy)-1,2-epoxypropane (1.34 g, 7.6 mmoles) was added in portions to a refluxed solution of 1-phenyl-3-(2-aminoethyl)hydantoin (1.75 g, 8 mmoles) in 50 ml of methanol.

Heating was continued for 5 additional hours. The mixture was evaporated and the crude product purified by silica gel column chromatography, eluting with

EXAMPLE 11

R-(+)-1-Phenyl-3-{2-[3-(2-cyanophenoxy)-2-hydroxypropyl]-aminoethyl}hydantoin Ic A mixture of (±) Ic (base) (3.94 g, 10 mmoles) and D-(−)-mandelic acid (1.52 g, 10 mmoles) was dissolved by heating in 30 ml of acetone. After cooling, the precipitated salt was filtered, m.p. 115°–118°, $[\alpha]_D$ (C=0.5, MeOH) = −24.3°, g 2.42. The product was crystallized again from 20 ml of acetone, obtaining a precipitate melting at 140°–141°, $[\alpha]_D$ (C=0.5, MeOH) = −19.67°.

A third crystallization from acetone gave 1.2 g of salt, m.p. 140°, $[\alpha]_D$ (C=0.5, MeOH) = −20°.

After treatment with 5% NaOH and extraction with chloroform the dextrorotatory isomer of Ic was obtained, 0.5 g, $[\alpha]_D$ (C=1, EtOH) = +3.49°.

Following substantially the same procedures described in the above reported examples, the following compounds were prepared:

1-phenyl-5-methyl-3-{2-[3-(2-cyanophenoxy)-2-hydroxypropyl]aminoethyl}hydantoin;
1-(3-methoxyphenyl)-5-methyl-3-{2-[3-(2-cyanophenoxy)-2-hydroxypropyl]aminoethyl}hydantoin;
1-(4-methoxyphenyl)-5-methyl-3-{2-[3-(2-cyanophenoxy)-2-hydroxypropyl]aminoethyl}hydantoin;

1-(3,4-dimethoxyphenyl)-5-methyl-3-{2-[3-(2-cyanophenoxy)-2-hydroxypropyl]aminoethyl}hydantoin;
1-(3-ethoxyphenyl)-3-{2-[3-(2-cyanophenoxy)-2-2-hydroxypropyl]aminoethyl}hydantoin
1-(4-ethoxyphenyl)-3-{2-[3-(2-cyanophenoxy)-2-hydroxypropyl]aminoethyl}hydantoin;
1-(3-methoxyphenyl)-3-{2-[3-(2-methylphenoxy)-2-hydroxypropyl]aminoethyl}hydantoin
1-(4-methoxyphenyl)-3-{2-[3-(2-methylphenoxy)-2-hydroxypropyl]aminoethyl}hydantoin
1-(4-chlorophenyl)-3-{2-[3-(2-methylphenoxy)-2-hydroxypropyl]aminoethyl}hydantoin;
1-(3,4-dimethoxyphenyl)-3-{2-[3-(2-methylphenoxy)-2-hydroxypropyl]aminoethyl}hydantoin;
1-(3,4-methylendioxyphenyl)-3-{2-[3-(2-methylphenoxy)-2-hydroxypropyl]aminoethyl}hydantoin;
1-(3-methoxyphenyl)-3-{2-[3-(2-chlorophenoxy)-2-hydroxypropyl]aminoethyl}hydantoin
1-(4-methoxyphenyl)-3-{2-[3-(2-chlorophenoxy)-2-hydroxypropyl]aminoethyl}hydantoin;
1-(4-chlorophenyl)-3-{2-[3-(2-chlorophenoxy)-2-hydroxypropyl]aminoethyl}hydantoin
1-(3,4-dimethoxyphenyl)-3-{2-[3-(2-chlorophenoxy)-2-hydroxypropyl]aminoethyl}hydantoin;
1-(3,4-methylendioxyphenyl)-3-{2-[3-(2-chlorophenoxy)-2-hydroxypropyl]aminoethyl}hydantoin;
1-(3-methoxyphenyl)-3-{2-[3-(2-allyloxyphenoxy)-2-hydroxypropyl]aminoethyl}hydantoin;
1-phenyl-3-{2-[3-(2-allyloxyphenoxy)-2-hydroxypropyl]aminoethyl}hydantoin.

PREPARATION OF THE STARTING COMPOUNDS

[A] 1-Phenyl-3-(2-aminoethyl)hydantoin

A solution of N-phenylglycine (Fluka) (30.2 g, 0.2 moles) in 900 ml of water and 1 ml of acetic acid was heated to 60° C. After thirty minutes potassium cyanate (16.2 g, 0.2 moles) in 100 ml of water was added. Heating was continued for 90', then 25 ml of 37% hydrochloric acid were added and the reaction mixture was heated for 15 h at 90° C. After cooling the precipitate was filtered and crystallized from 95% ethanol. 8.65 g of 1-phenylhydantoin were obtained, m.p. 197°–198°.

2-Bbromoethylamine hydrobromide (24.6 g, 0.12 moles) was added to a solution of 1-phenylhydantoin (21.35 g, 0.12 moles) and potassium hydroxide (16.65 g, 0.25 moles) in 600 ml of absolute ethanol at 90° C. The reaction mixture was refluxed for 48 h, cooled, the salts were filtered, and evaporated.

The residue was treated with aqueous hydrochloric acid and washed with chloroform. The aqueous phase was alkalinized by sodium bicarbonate and extracted with chloroform. After solvent evaporation the title compound was obtained, 13 g, yield 50%, m.p. 151°–153°.

[B] 1-(4-Chlorophenyl)-3-(2-aminoethyl)hydantoin

In the same way as in [A]0 and reacting the N-(4-chlorophenyl)-glycine (42.2 g, 0.227 moles) with potassium cyanate (18.4 g, 0.227 moles) the 1-(4-chlorophenyl)hydantoin was obtained, m.p. 234°–236° C.

By reacting the latter (19.6 g, 93 mmoles) with 2-bromoethylamine hydrobromide (19.05 g, 93 mmoles) as described in [A] the title compound was obtained, m.p. 142°–145° C.

[C] 1-(3,4-Dimethoxyphenyl)-3-(2-aminoethyl)hydantoin

In the same way as in [A] and reacting the N-(3,4-dimethoxyphenyl)glycine (17.2 g, 81 mmoles) with potassium cyanate (6.6 g, 81 mmoles) the 1-(3,4-dimethoxyphenyl)hydantoin was obtained, m.p. 223°–225° C. By reacting the latter (11.23 g, 47.5 mmoles) with 2-bromoethylamine hydrobromide (9.74 g, 47.5 mmoles) as described in [A] the title compound was obtained, m.p. 162°–164° C.

[D] 1-(4-Methoxyphenyl)-3-(2-aminoethyl)hydantoin

In the same way as in [A] and reacting the N-(4-methoxyphenyl)glycine (71.87 g, 396 mmoles) with potassium cyanate (38.7 g, 595 mmoles) the 1-(4-methoxyphenyl)hydantoin was obtained, m.p. 197°–198° C.

By reacting the latter (20.62 g, 100 mmoles) with 2-bromoethylamine hydrobromide (20.49 g, 100 mmoles) as described in [A] the title compound was obtained, m.p. 143°–146° C.

[E] 1-(3,4-methylendioxyphenyl)-3-(2-aminoethyl)hydantoin

In the same way as in [A] and reacting the N-(3,4-methylendioxyphenyl)glycine ethyl ester (16.8 g, 75 mmoles) with potassium cyanate (9.16 g, 113 mmoles) the 1-(3,4-methylendioxyphenyl)hydantoin was obtained, m.p. 241°–243° C.

By reacting the latter (6 g, 27 mmoles) with 2-chloroethylamine hydrochloride (3.8 g, 32.7 mmoles) as described in [A] the title compound was obtained, m.p. 171°–173° C.

[F] 1-(3-Methoxyphenyl)-3-(2-aminoethyl)hydantoin

In the same way as in [A] and reacting the N-(3-methoxyphenyl)glycine ethyl ester (26 g, 124 mmoles) with potassium cyanate (15.13 g, 186 mmoles) the 1-(3-methoxyphenyl)hydantoin was obtained, m.p. 107°–108° C.

By reacting the latter (6 g, 29 mmoles) with 2-chloroethylamine hydrochloride (4.5 g, 35 mmoles) as described in [A] the title compound was obtained, m.p. 127°–129° C.

[G] 1-Phenyl-3-(2-bromoethyl)hydantoin

A mixture of 1-phenylhydantoin (5 g, 28.3 mmoles), 85% potassium hydroxide (2.06 g, 31.2 mmoles), 1,2-dibromoethane (11.72 g, 62.4 mmoles) and potassium iodide (catalytic amounts) in 100 ml of ethanol was refluxed for 67 hours. The solid was filtered, the mother liquors were evaporated and the crude product was purified by silica gel column chromatography eluting with increasing mixtures of ethyl acetate in hexane. By crystallization from acetone/hexane 1.56 g of the title compound were obtained, m.p. 146°–147° C.

[H] (R)-(−)-3-(2-Cyanophenoxy)-1,2-epoxypropane

2-Cyanophenol (8.12 g, 68.1 mmoles) was added to a suspension of sodium hydride (3.27 g, 68.1 mmoles) in 70 ml of anhydrous dimethylformamide.

When the hydrogen evolution was over, a solution of (R)-(−)-2,2-dimethyl-4-tosyloxymethyl-1,3-dioxolane [Chem. Pharm. Bull. 29, 3593 (1981)], (19.5 g, 68.1 mmoles) in 70 ml of dimethylformamide, was added dropwise. The mixture was heated to 130° for 3 hours, poured in ice and extracted with ether, and the organic phase was then washed with 1.5% NaOH and with water.

The organic phase was then dried and evaporated, yielding 9.7 g of S-(+)-4-(2-cyanophenoxymethyl)-2,2-dimethyl-1,3-dioxolane as yellow oil, yield 84.8%, $[\alpha]_D$ (C=1, EtOH)= +28.4°.

40% Hydrobromic acid in acetic acid (22 ml, 160.5 mmoles) was added dropwise to a solution of the latter compound (10.7 g, 45.9 mmoles) in 18 ml of acetic acid, cooled at 0° C. The mixture was stirred for 5 hours at room temperature, thereafter water, ether and sodium bicarbonate were added up to neutrality. The organic phase was separated, dried and evaporated.

13.6 G of (S)-(+)-(2-cyanophenoxy)-2-acetoxy-1-bromopropane were obtained as oil, yield 99.4%, $[\alpha]_D$ (C=1, EtOH)= +15.16°.

A solution of (S)-(+)-3-(2-cyanophenoxy)-2-acetoxy-1-bromopropane and cetyltrimethyl ammonium bromide (2.54 g) in 130 ml of methylene chloride was added to 130 ml of 10% sodium hydroxide and the mixture was stirred for 15 hours. The phases were separated, the organic phase was washed with a saturated sodium chloride solution, dried and evaporated. The crude product was purified by silica gel column chromatography, eluting with cyclohexane/methylene chloride.

2.77 g of the title compound were obtained, m.p. 84°-86°, $[\alpha]_D$ (C=1, EtOH)= -16.07°.

[I] (S)-(+)-3-(2-cyanophenoxy)-1,2-epoxypropane

In the same way as in [H] but reacting 2-cyanophenol (7.1 g, 59.7 mmoles) with (S)-(+)-2,2-dimethyl-4-tox-yloxymethyl-1,3-dioxolane (J. Org. Chem. 42, 1006 (1977)) (17.1 g, 59.7 mmoles) the (R)-(−)-4-(2-cyanophenoxymethyl)-2,2-dimethyl-1,3-dioxolane with $[\alpha]_D$ (C=1, EtOH)= -30.18°, was obtained. The reaction of this compound (13.9 g, 59.6 mmoles) with 40% hydrobromic acid in acetic acid yields (R)-(−)-3-(2-cyanophenoxy)-2-acetoxy-1-bromopropane with $[\alpha]_D$ (C=1, EtOH)= -15.9°.

Finally, starting from this compound and carrying out the reaction as described in the third and last step of [H], the title compound was obtained $[\alpha]_D$ (C=1, EtOH)= +17.69°.

The pharmacological activity of the compounds of the invention was evaluated by determining the acute toxicity, the in vitro and in vivo β-blocking activity.

I.V. TOXICITY IN MICE

Charles River male CD$_1$ mice, weighing 25 g were used. The administration volume of the compounds, solubilized in H$_2$O and exceptionally in dimethylsulfoxide, was 0.02 ml/10 g of body weight.

The LD$_{50}$ after 7 days was calculated according to the method of Litchfield and Wilcoxon (J. Pharm. Exp. Ter. 96, 99, 1949).

In vitro β-blocking activity

Hartley albino guinea pigs of 450 g average weight were used. The atria and the trachea have been suspended respectively in Ringer oxygenated solution at 32° C., and in Krebs carboxygenated solution medicated with pilocarpine, at 37° C. (J. Pharmacol. 66, 455P, 1979).

After 30' minute stabilization the samples were stimulated with a single submaximal concentration of isopropylnoradrenaline (INA) ($10^{-8}$M for the atria and $10^{-7}$M for the trachea) in the absence or presence of different antagonist's concentrations.

The percent inhibitions of the chronotropic and positive inotropic effect (atria) and of relaxation (trachea) were evaluated and the IC$_{50}$ values were calculated therefrom.

β-BLOCKING ACTIVITY ON CONSCIOUS RATS, I.V.

Male Wistar rats, weighing 250-350 g (from Charles River) whose common left carotid artery and the right jugular vein were chronically catheterized under sodium Pentobarbital anaesthesia (35 mg/kg, i.p.) (J. Pharm. Pharmacol. 34, 442, 1982), have been used. The arterial pressure (AP) and heart rate (HR) were graphically recorded on a type R. multichannel Beckman poligraph.

I.V. administrations of a single and submaximal dose of INA (0.12-0.16 mg/kg) were carried out before and after the i.v. treatment with a β-blocker of the present invention and the percent inhibition of the INA positive chronotropic effect ($\beta_1$) as described by Kreighbaum (J. Med. Chem. 23, 285, 1980) was evaluated.

As reference compounds four β-blocking drugs, widely utilized in therapy, were used: atenolol, labetalol, propranolol and metoprolol.

From the results, reported in Table II, it is evident how the compounds of the invention, in addition to a relatively low toxicity, are endowed with an high β-adrenolytic action, with a much higher specificity for the myocardial $\beta_1$ receptors than for the peripheric ones ($\beta_2$), typical of the bronchial, tracheal and vascular tissues.

Moreover it must be pointed out that the $\beta_1$ blocking activity in conscious rats, because of the high cardioselectivity degree, could be undervalued because of residual reflex tachycardia due to the non-blocked $\beta_2$ hypotensive stimulus. This phenomenon has been already described in literature (Br. J. Pharmacol., 251P, 1982).

The cardioselectivity is a particularly desirable property in a β-blocking drug which can be thus used also in asthmatic patients or in patients suffering troubles in the peripheral circulation and it could turn out also to be more indicated even in the treatment of hypertension because it does not block the peripheral $\beta_2$ vascular receptors mediating the vasodilation.

TABLE II

In vitro β-blocking activity (guinea pigs atria and trachea) and in vivo (conscious rat i.v.) and acute toxicity (mice i.v.)

| Compound | Toxicity Mice i.v. LD$_{50}$ (mg/kg) | β-Blocking activity (% inhib. isoproterenol) Vitro: IC$_{50}$ (M)$^{(a)}$ | | | Vivo inhib. %$^{(b)}$ |
|---|---|---|---|---|---|
| | | Atria | | | Conscious rat i.v.$^{(c)}$ chronotropism β$_1$ |
| | | Chronotropism × 10$^{-7}$ | β$_1$ Inotropism × 10$^{-7}$ | Trachea β$_2$ × 10$^{-7}$ | |
| Ia | 96 (93–99) | 1.4 | 4.3 | 67 | 59 |
| Ib | 69 (61–77) | 4.3 | 9.4 | 62 | 50 |
| Ic | 99 (91–107) | 1.2 | 0.9 | 20 | 67 |
| Id | 45 (40–56) | 7.7 | 12 | >100 | 18 |
| Ie | 25 (22–29) | >100 | >100 | >100 | 19 |
| If | 70 (65–78) | 2.1 | 2.7 | 60 | 68 |
| Ig | 126 (120–132) | 2.3 | 2.1 | 15 | 53 |
| Ih | 111 (106–116) | 4.6 | 8.9 | 11 | 58 |
| Ii | 137 (126–159) | 0.82 | 1.9 | 4.3 | 70 |
| Il | 135 | 0.45 | 0.96 | 3.6 | n.d. |
| Im | 132 | 0.41 | 0.63 | 7.8 | n.d. |
| In | 120 | 0.76 | 1.3 | 6.4 | n.d. |
| Io | 60 | 1.15 | 1.5 | 16 | n.d. |
| Ip | 80 | 0.54 | 1.15 | 6 | n.d. |
| Ic(R) | | 14 | 34 | >1000 | n.d. |
| Ic(S) | | 0.29 | 0.6 | 6 | n.d. |
| Propranolol | 36 (32–40) | 0.6 | 12 | 0.79 | 73 |
| Labetalol | 55 (52–59) | 2.4 | 2.1 | 11 | 82 |
| Atenolol | 85 (78–93) | 15 | 17 | 57 | n.d. |
| Metoprolol | 103 (94–113) | 3.1 | 2.9 | 10 | 60 |

$^{(a)}$3–4 concentrations: 2–3 runs for each concentration
$^{(b)}$2 rats each compound; $^{(c)}$administered at 1 mg/kg except Ia–c (3 mg/kg) and propranolol (0.1 mg/kg).

Moreover, by way of example, some of the compounds of the present invention have been subjected to a deep examination in order to biochemically characterize, by means of the receptorial binding method, the affinity for the β-adrenergic receptors and the specificity for said receptorial site.

For this purpose, the concentrations values of Ic, Ii and some reference compounds, able to inhibit 50% (IC$_{50}$) of the binding of the different $^3$H ligands specific for the receptorial populations under study, have been evaluated.

It has been particularly evaluated the affinity of the compounds Ic and Ii and of the reference compounds for the β$_1$ and β$_2$ receptors.

The experiments have been carried out according to the method described by U. Prichard et al. in J. Biol. Chem. 253 (1978), 5090 and the results are shown in the following Table III.

TABLE III

Molar IC$_{50}$ values of inhibition of H$^3$—DHA (Dihydroalprenolol) binding to β$_1$ and β$_2$ adrenergic binding and cardioselectivity index

| Product | IC$_{50}$ β$_1$ | IC$_{50}$ β$_2$ | Cardioselectivity IC$_{50}$ β$_1$/IC$_{50}$ β$_2$ |
|---|---|---|---|
| Ic | 6.7 × 10$^{-9}$ | 9.3 × 10$^{-6}$ | 1388.0 |
| Ii | 9.2 × 10$^{-9}$ | 4 × 10$^{-7}$ | 43.5 |
| Metoprolol | 1 × 10$^{-7}$ | 2.3 × 10$^{-6}$ | 23.0 |
| Propranolol | 3.7 × 10$^{-9}$ | 4.8 × 10$^{-9}$ | 1.3 |
| Zinterol | 5.5 × 10$^{-7}$ | 1.6 × 10$^{-9}$ | 0.029 |

The data shown in the above Table clearly show that the compounds of the present invention, which prove to be selectively active molecules at the adrenergic system, have particularly affinity for the β$_1$ receptorial sub-type, showing therefore particularly high cardioselectivity characteristics.

In fact, the affinity of compounds Ic and Ii for the β$_2$ receptors is remarkably lower than the one shown for β$_1$ receptors, showing therefore a remarkably higher cardioselectivity degree than that of the reference compounds.

From the above reported data, it is evident that the compounds of the invention can be effectively used in the prophylaxis and therapy of cardiac diseases, angina pectoris, arrythmias, in the treatment of hypertension, and in the prevention of reinfarction.

The present invention concerns also all the industrial aspects connected with the therapeutical use of the compounds of formula I or their salts as drugs having β-adrenolytic action.

An essential aspect of the invention is therefore provided by pharmaceutical formulations containing as the active principle therapeutically effective amounts of compounds I or salts thereof together with suitable carriers and excipients.

For the use as drugs with β-adrenolytic action, the compounds of the invention can be administered both by the oral and by the parenteral (preferably intravenous) route. Dosage forms suitable for the administration by the oral route comprise capsules, tablets, sugar-coated tablets, granules, syrups and solutions, whereas, for the parenteral administrations, suitable dosage forms are the sterile injectable solutions.

Said dosage forms are prepared by compounding the active ingredients of formula I with a suitable carrier, excipients, binders, preservatives, stabilizers, flavouring agents or the like as called for by acceptable pharmaceutical practice.

Moreover, the compounds of the present invention can also be formulated with other pharmaceutically active ingredients.

The capsules, tablets, sugar-coated tablets and granules can comprise particularly excipients such as lactose, calcium phosphate, mannitole, starch, caoline, etc., binding agents such as adraganth gum, gelatine, maize starch etc., lubricant agents such as magnesium stearate, talc, calcium stearate etc., disgregating agents such as alginic acid, maize starch etc., natural or synthetic sweetening agents, flavouring agents, and coloring agents.

The syrups and oral solutions may contain in addition to the active principle dissolved in water or in an aqueous vehicle, saccharose as sweetening agent, methyl- and propylparaben as preservative, coloring and sweetening agents.

Different other substances can also be used in addition or in substition of above cited ones, as known by anyone skilled in pharmaceutical technique.

It should be noted that, even if not specifically described herein, all these pharmaceutical compositions are comprised within the scope of the present invention.

In the case of oral administration, the suggested daily dosage will range, according to diagnosed pathology, the severeness of the clinical situation and the patient's weight and age, from 30 to 600 milligrams, optionally divided in 2-4 administrations. Preferred unit dosage forms will comprise therefore from 10 to 400 mg of active ingredient. In the case of administration by the intravenous route, lower dosages, ranging generally from 1 mg to 20 mg a day, are of course necessary. Preferred dosage forms in the case of intravenous administration will contain from 0.5 to 3 mg of active principle per volume unit.

We claim:

1. A compound of formula I,

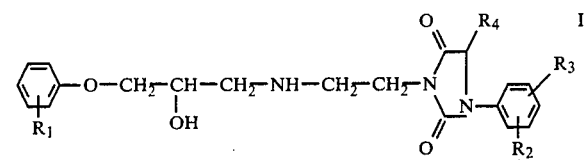

in the form of racemic mixture, of separated optical isomers and, when $R_4$ is different from hydrogen, of diastereoisomeric couples optionally separated and resolved in the enantiomers wherein:

$R_1$ is hydrogen, lower alkyl, lower alkoxy, alkylenoxy, halogen, cyano, carboxyamido or uredio group optionally separated from the phenyl ring by a methylene or ethylene bridge;

$R_2$ is hydrogen, halogen, lower alkyl or alkoxy;

$R_3$ is hydrogen, halogen, lower alkyl, lower alkoxy or $R_2$ and $R_3$, taken together, are a methylendioxy group;

$R_4$ is hydrogen or lower alkyl, and their pharmaceutically active acceptable salts.

2. A compound according to claim 1 wherein $R_1$ is hydrogen, lower alkyl, an halogen atom or a cyano group, and $R_4$ is hydrogen.

3. A compound according to claim 1 wherein $R_2$ is hydrogen.

4. A compound according to claim 3 wherein $R_1$ is a cyano, methyl or chloro group in position 2.

5. A compound according to claim 4 wherein $R_1$ is a cyano group.

6. A compound according to claim 5 which is 1-phenyl-3-{2-[3-(2-cyanophenoxy)-2-hydroxypropyl]aminoethyl}hydantoin.

7. A compound according to claim 6 in optically pure form.

8. Pharmaceutical compositions having β-adrenolytic activity for the oral or parenteral administration of therapeutically active amounts of the compounds of formula I or their salts, together with suitable carriers and excipients, in form of tablets, capsules, granules, syrups, solutions, vials and sterile injectable bottles.

9. A pharmaceutical composition as in claim 8 containing from 10 to 400 mg of a compound of formula I per unit dose, in the case of oral administation, and from 0.5 to 3 mg per unit volume in the case of parenteral administration.

* * * * *